(12) United States Patent
Gustafsson et al.

(10) Patent No.: US 9,539,395 B2
(45) Date of Patent: Jan. 10, 2017

(54) MEDICAMENT DELIVERY DEVICE

(75) Inventors: Magnus Gustafsson, Tullinge (SE); Stefan Lööf, Sköndal (SE)

(73) Assignee: SHL Group AB, Nacka Strand (SE)

( * ) Notice: Subject to any disclaimer, the term of this patent is extended or adjusted under 35 U.S.C. 154(b) by 495 days.

(21) Appl. No.: 13/878,809

(22) PCT Filed: Oct. 7, 2011

(86) PCT No.: PCT/SE2011/051202
§ 371 (c)(1),
(2), (4) Date: Apr. 11, 2013

(87) PCT Pub. No.: WO2012/050511
PCT Pub. Date: Apr. 19, 2012

(65) Prior Publication Data
US 2013/0197446 A1    Aug. 1, 2013

Related U.S. Application Data

(60) Provisional application No. 61/391,733, filed on Oct. 11, 2010.

(30) Foreign Application Priority Data

Oct. 11, 2010    (SE) ...................... 1051064

(51) Int. Cl.
*A61M 5/315*    (2006.01)
(52) U.S. Cl.
CPC ...... *A61M 5/31511* (2013.01); *A61M 5/31595* (2013.01); *A61M 5/31505* (2013.01)
(58) Field of Classification Search
CPC ............. A61M 2005/3125; A61M 2005/3126; A61M 5/31551; A61M 2205/6063; A61M 2205/6081; A61M 5/31535; A61M 2205/60; A61M 2205/584; A61M 5/3155; A61M 2005/2073; A61M 5/31541; A61M 5/31583; A61M 5/31505; A61M 5/31511; A61M 5/31595; A61M 5/31593; A61M 5/31573
(Continued)

(56) References Cited

U.S. PATENT DOCUMENTS 1,393,720 A  * 10/1921 Lomas .............. A61M 5/31595
                                                  12/142 N
4,475,905 A  * 10/1984 Himmelstrup .... A61M 5/31551
                                                  604/208
(Continued)

FOREIGN PATENT DOCUMENTS

EP    0611035 A1 *  8/1994    ............ A61M 5/315
EP    0611035 A1    8/1994

OTHER PUBLICATIONS

Swedish Patent Office, Int'l Search Report in PCT/SE2011/051202, Jan. 26, 2012.
(Continued)

*Primary Examiner* — Nathan R Price
*Assistant Examiner* — Weng Lee
(74) *Attorney, Agent, or Firm* — Piedmont Intellectual Property

(57) ABSTRACT

Provided is a medicament delivery device comprising an axially elongated housing, a coaxially extending plunger rod mounted with in the housing for expelling successive doses of medicament and rotateable about the axis. The plunger rod can be axially displaced from a ready-to-use position for expelling a dose of medicament to a non-ready-to-use position axially spaced from said ready-to-use position along the axis, and from said non-ready-to use position to a subsequent ready-to-use position angularly spaced from said non-ready-to use position about the axis The device further comprises an indicator member displaceably mounted onto the housing between a first angular position indicative of the
(Continued)

ready-to-use positions and a second angular position indicative of the non-ready-to use positions.

20 Claims, 7 Drawing Sheets

(58) Field of Classification Search
USPC .................................. 608/187, 189, 207–211
See application file for complete search history.

(56) References Cited

U.S. PATENT DOCUMENTS

| | | | |
|---|---|---|---|
| 4,810,249 A | | 3/1989 | Haber et al. |
| 5,318,544 A | | 6/1994 | Drypen et al. |
| 5,591,136 A | * | 1/1997 | Gabriel .............. A61M 5/31553 |
| | | | 604/208 |
| 7,695,454 B2 | * | 4/2010 | Barron .............. A61M 5/31541 |
| | | | 604/187 |
| 8,851,339 B2 | * | 10/2014 | Schultz .............. B65D 83/0005 |
| | | | 222/327 |
| 9,022,993 B2 | * | 5/2015 | Dasbach ............. A61M 5/3156 |
| | | | 604/211 |
| 2002/0010431 A1 | | 1/2002 | Dixon et al. |
| 2003/0089743 A1 | * | 5/2003 | Py .......................... A45D 40/26 |
| | | | 222/386 |
| 2003/0158523 A1 | * | 8/2003 | Hjertman .......... A61M 5/31553 |
| | | | 604/207 |
| 2008/0077095 A1 | | 3/2008 | Kirchhofer |
| 2009/0275916 A1 | * | 11/2009 | Harms et al. ................. 604/506 |
| 2010/0036320 A1 | * | 2/2010 | Cox et al. ..................... 604/135 |
| 2012/0296286 A1 | * | 11/2012 | Raab ................. A61M 5/31593 |
| | | | 604/211 |

OTHER PUBLICATIONS

Swedish Patent Office, Written Opinion in PCT/SE2011/051202, Jan. 26, 2012.

* cited by examiner

MEDICAMENT DELIVERY DEVICE

TECHNICAL FIELD

The present invention relates to a medicament delivery device and more particularly to a medicament delivery device comprising a support mechanism for easily indicating the enablement or disablement of the device when a user aims to eject a predetermined volume of medicament.

BACKGROUND

Traditionally with a conventional hypodermic syringe a practitioner, or user, must stop depressing a plunger based on visual feedback, typically from a scale on the hypodermic syringe. Consequently, it is difficult to perform a repeated dose injection with a high degree of accuracy and/or precision.

In U.S. Pat. No. 5,318,544 is disclosed a syringe for metering precise volumes of fluid without having to use a visual volumetric scale. The document discloses a syringe container adapted for receiving a plunger containing a plurality of stop surfaces which are angularly and linearly displaced about a longitudinal axis of said plunger. Translation of the plunger brings a first stop surface into contact with a stop edge of the syringe container. The plunger is then rotated to release the first stop surface from the stop edge, thereby permitting the plunger to be translated until a second stop surface contacts the stop edge. During translation of the plunger, a predetermined volume of fluid is metered through an orifice. This allows a user to administer predetermined volumes of fluid, precisely metered through the orifice, without having to read a scale of volumetric units and without requiring the user having to control the stopping action of the plunger.

The disclosed prior art lacks of indicator means. The lack of indicator means confuses a user to know whether or not the medicament delivery device is ready to use.

There is therefore a need for an arrangement that can provide both expelling repeated doses in a precise, easy and controlled manner having means for easily indicating the enablement or disablement of the device when a user aims to eject a predetermined volume of medicament. Thus, as can be noted, human handling aspects of a medicament delivery device are crucial and there are several rationales for improving existing solutions.

SUMMARY

The aim of the present invention is to utilize the advantages of integrating a support mechanism that improve the disadvantage of known prior art.

According to a main aspect of the invention, it is characterised by a medicament delivery device comprising an elongated housing extending along an axis for containing a medicament, a coaxially extending plunger rod which is mounted within the housing so as to be axially displaceable for expelling successive doses of medicament and able to rotate about the axis, the plunger rod and the housing respectively comprising first and second guiding means in mutual engagement which are adapted to guide the plunger rod within the housing successively from a ready-to-use position, wherein the plunger rod can be axially displaced for expelling a dose of medicament, to a non-ready-to use position, wherein the plunger rod is axially blocked, said non-ready-to use position being axially spaced from said ready-to-use position; and from said non-ready-to use position to a subsequent ready-to-use position angularly spaced from said non-ready-to use position about the axis, wherein the device further comprises an indicator member displaceably mounted onto the housing between a first angular position indicative of the ready-to-use positions and a second angular position indicative of the non-ready-to use positions, the indicator member and the plunger rod respectively comprising third and fourth guiding means in mutual engagement whereby the position of the indicator member is linked to the position of the plunger rod.

According to another aspect of the invention, the indicator member comprises indicator means on its outer surface for enabling visual and/or audible and/or tactile indication through a window/opening on the housing when the plunger rod is in the ready-to-use positions or in the non-ready-to-use positions.

According to yet another aspect of the invention, the indicator means comprises a colour mark and/or a flexible protrusion.

According to a further aspect of the invention, the indicator member is resiliently connected to the housing through at least one resilient member which comprises a first end connected to the indicator member and a second end connected to the housing.

According to yet a further aspect of the invention, the indicator is mounted onto the housing so as to be rotatable about the axis between the first angular position indicative of the ready-to-use positions and the second angular position indicative of the non-ready-to-use positions, the indicator member being biased by the resilient member into the second angular position.

According to another aspect of the invention, the second guiding means is at least one inward radial extending protrusion and the third guiding means is also at least one inward radial extending protrusion.

According to yet another aspect of the invention, the third guiding means is arranged to serve as a backup for the second guiding means.

According to a further aspect of the invention, the axially displaced distance of the plunger rod between a ready-to-use position and a non-ready-to-use position corresponds to a precise volume of medicament to be expelled.

According to yet a further aspect of the invention, the first and fourth guiding means are formed by distinct axially extending grooved and staggered tracks formed by alternating axial sections and circumferential sections extending in radial planes, said axial sections corresponding to the ready-to-use positions.

According to another aspect of the invention, the plunger rod comprises an outer circumferential surface divided into a first and a second circumferential halve surfaces, wherein the first guiding means is arranged on the first circumferential half surface and wherein the fourth guiding means is arranged opposite to the first guiding means on the second circumferential half surface.

According to yet another aspect of the invention, each axially extending grooved and staggered track form a continuous square wave pattern.

According to a further aspect of the invention, the first and fourth guiding means are formed by a single axially extending grooved and staggered track formed by alternating axial sections and circumferential sections extending in radial planes, said axial sections corresponding to the ready-to-use positions.

According to yet a further aspect of the invention, the plunger rod comprises an outer circumferential surface and wherein the single axially extending grooved and staggered track is continuously arranged around said outer circumferential surface.

According to another aspect of the invention, the single axially extending grooved and staggered track has a continuous spiral stair pattern.

According to yet another aspect of the invention, the medicament delivery device consists of an injection device.

By the disclosed medicament delivery device, unintentional actuation of the medicament delivery device is avoided and at the same time precise doses of medicament can be delivered together with clear indication means, indicating when the medicament delivery device is activated or closed. These and other aspects of and advantages with the present invention will become apparent from the following detailed description and from the accompanying drawings.

BRIEF DESCRIPTION OF THE DRAWINGS

In the following description of embodiments of the invention, reference will be made to the accompanying drawings of which.

DETAILED DESCRIPTION

Figure 1:
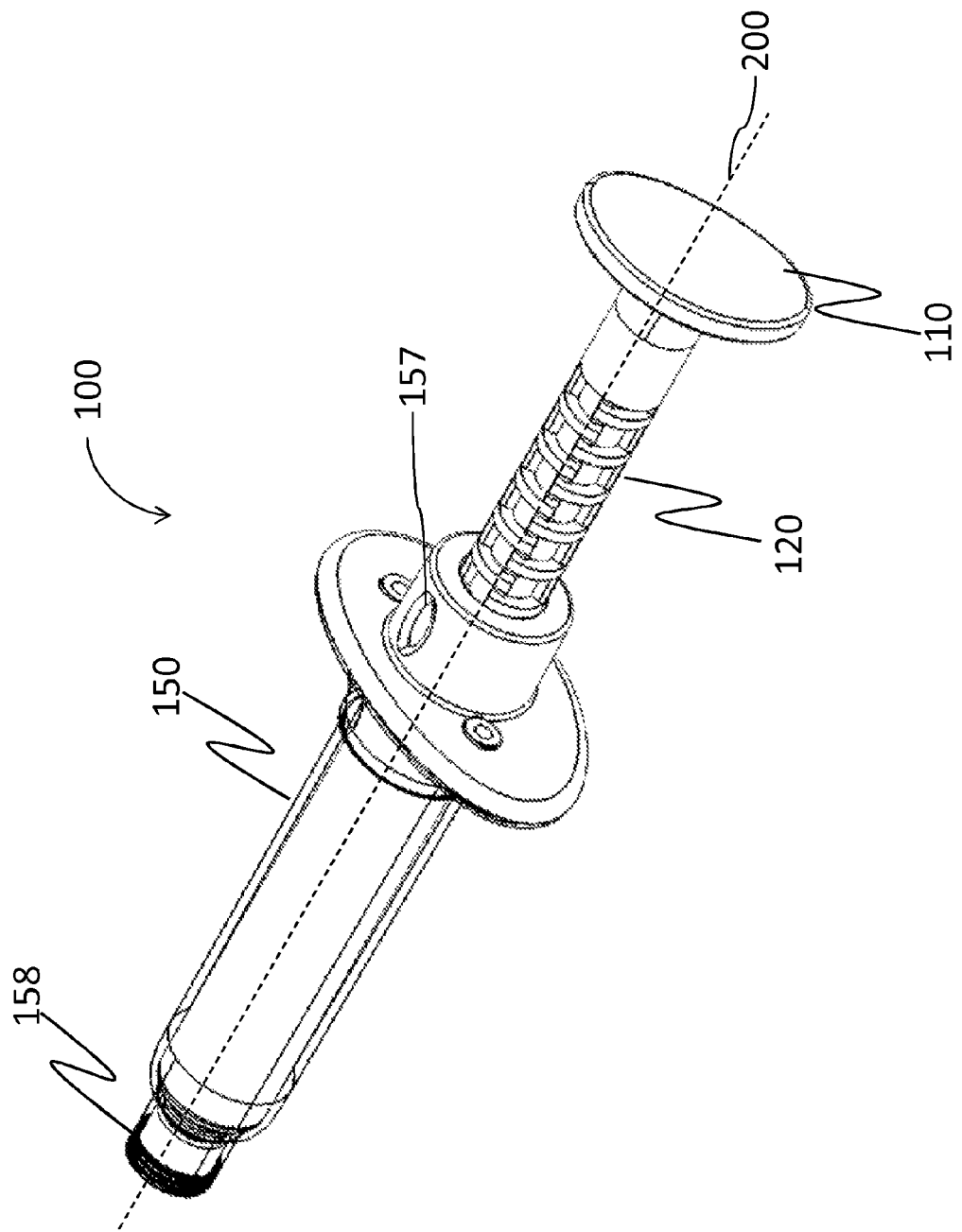
FIG. 1 is a perspective view of an exemplary embodiment of the medicament delivery device in the present invention.

As should be noted in present application, when the term "distal part/end" is used, this refers to the part/end of the delivery device, or the parts/ends of the members thereof, which is/are located the furthest away from the medicament delivery site of the patient. Correspondingly, when the term "proximal part/end" is used, this refers to the part/end of the delivery device, or the parts/ends of the members thereof, which, is/are located closest to the medicament delivery site of the patient.

The present invention relates to a medicament delivery device comprising an elongated housing 150 extending along an axis 200 for containing a medicament, a coaxially extending plunger rod 120; 220 which is mounted within the housing 150 so as to be axially displaceable for expelling successive doses of medicament and able to rotate about the axis 200, the plunger rod 120; 220 and the housing 150 respectively comprising first 123; 222 and second 154 guiding means in mutual engagement which are adapted to guide the plunger rod 120; 220 within the housing 150 successively from a ready-to-use position, wherein the plunger rod 120; 220 can be axially displaced for expelling a dose of medicament, to a non-ready-to use position, wherein the plunger rod 120; 220 is axially blocked, said non-ready-to use position being axially spaced from said ready-to-use position; and from said non-ready-to use position to a subsequent ready-to-use position angularly spaced from said non-ready-to use position about the axis 200.

The device of the present invention further comprises an indicator member 160 displaceably mounted onto the housing 150 between a first angular position indicative of the ready-to-use positions and a second angular position indicative of the non-ready-to use positions, the indicator member 16) and the plunger rod 120; 220 respectively comprising third 161 and fourth 124; 222 guiding means in mutual engagement whereby the position of the indicator member 160 is linked to the position of the plunger rod.

In the present invention, the indicator member 160, which is a tubular formed component, comprises indicator means 180 on its outer surface for enabling visual and/or audible and/or tactile indication through a window/opening 157 on the housing when the plunger rod is in the ready-to-use positions or in the non-ready-to-use positions. The indicator member is arranged to resiliently co-act with the housing through at least one resilient member 170 which comprises a first end 171 connected to the movable indicator member and a second end 172 connected to the housing. Further, the indicator member is mounted onto the housing so as to be rotatable about the axis 200 between the first angular position indicative of the ready-to-use positions and the second angular position indicative of the non-ready-to-use positions, the indicator member being biased by the resilient member into the second angular position.

In the exemplary embodiments of the invention, the second guiding means is e.g. at least one inward radial extending protrusion 154 and the third guiding means is also e.g. at least one inward radial extending protrusion 161.

FIG. 1 is a perspective view of an exemplary embodiment of the medicament delivery device 100. In FIG. 1 is illustrated the axis 200 which is a longitudinal axis. The longitudinal extending plunger rod 120 illustrated in FIG. 1 comprises an actuator member 110, and the housing 150 comprises at least one window/opening 157 on its side circumferential surface and proximal engagement means 158 as e.g. threads for engaging a delivery member as e.g. a needle to the device.

Figure 2:
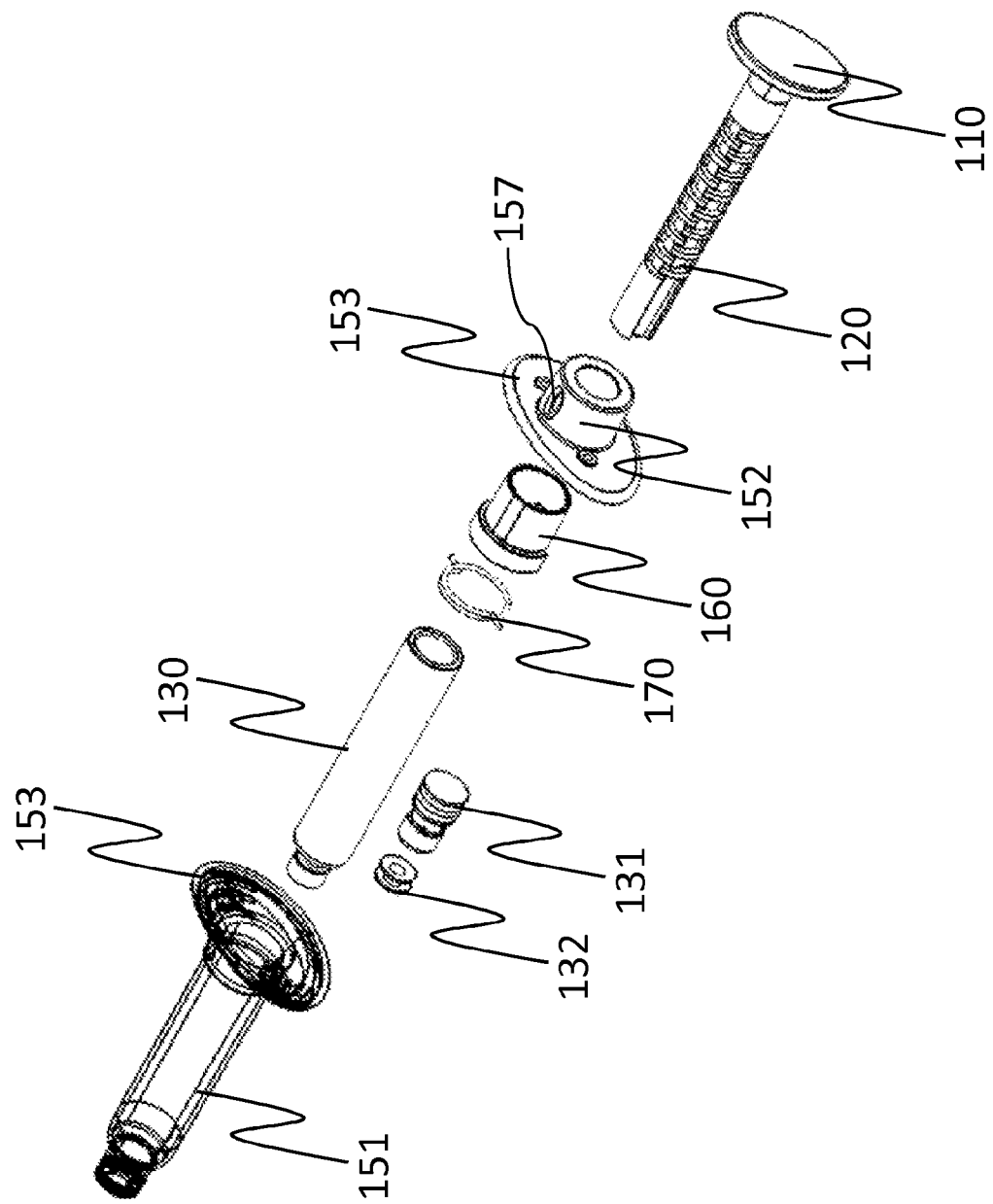
FIG. 2 is a perspective view of exemplary components of the exemplary embodiment of the medicament delivery device in the present invention.

FIG. 2 is a perspective view of exemplary components of the exemplary embodiment of the medicament delivery device disclosed in FIG. 1. In FIG. 2 is illustrated the actuator member 110 and the plunger rod 120. Furthermore is disclosed the housing 150 which is divided in two parts: a tubular proximal housing part 151 and a tubular distal housing part 152, both parts comprising a shield member 153 configured to fixedly attach the two housing parts by suitable fixing means known in the art as e.g. bayonet fittings. The housing 150 is adapted to accommodate a medicament container 130 as e.g. a cartridge. Said cartridge as illustrated in FIG. 2 comprises a slidable stopper 131 and a septum 132. Furthermore is illustrated the movable indicator member 160 and the at least one resilient member 170.

Figure 3:
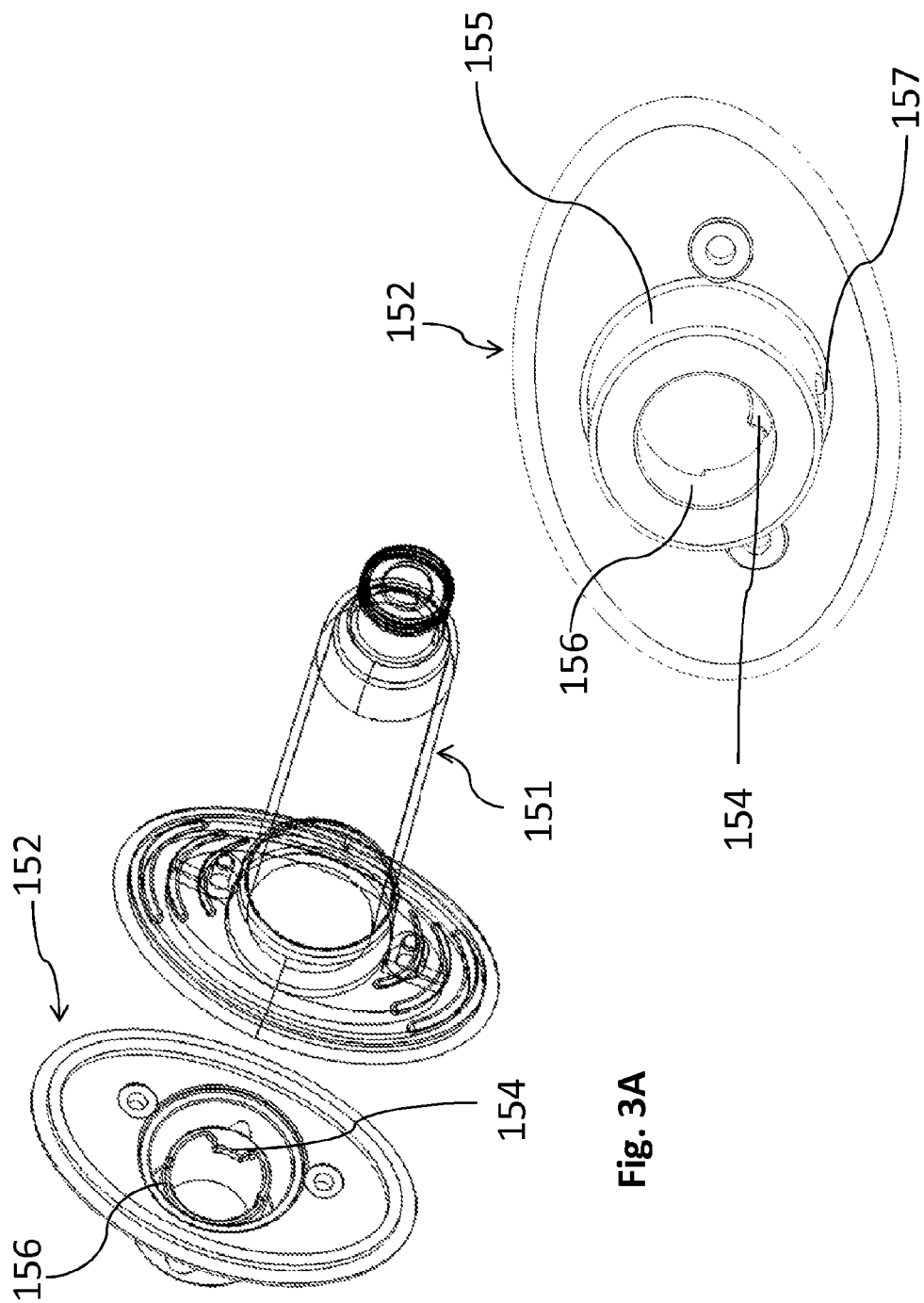
FIG. 3A is a detail perspective bottom view of an example of a housing.
FIG. 3B is detail perspective top view of FIG. 3A.

FIG. 3A is a detail perspective bottom view of the tubular distal housing part 152 illustrating the second guiding means 154 of the housing, which is an inward radial extending protrusion. The tubular distal housing part 152 comprises a first tubular distal housing part 155 and a second tubular distal housing part 156 connected to each other by an annular plate and wherein the second tubular distal housing part 156 is coaxially arranged within the first tubular distal housing part 155 forming a first annular channel. The second guiding means 154, which is an inward radial extending protrusion, is arranged on the proximal inner circumferential surface of the second tubular distal part 156 and the opening/window 157 is arranged on the circumferential surface of the first tubular distal housing part 155. FIG. 3B is a detail perspective top view of the tubular distal housing part 152 illustrating the same second guiding means 154.

Figure 4:
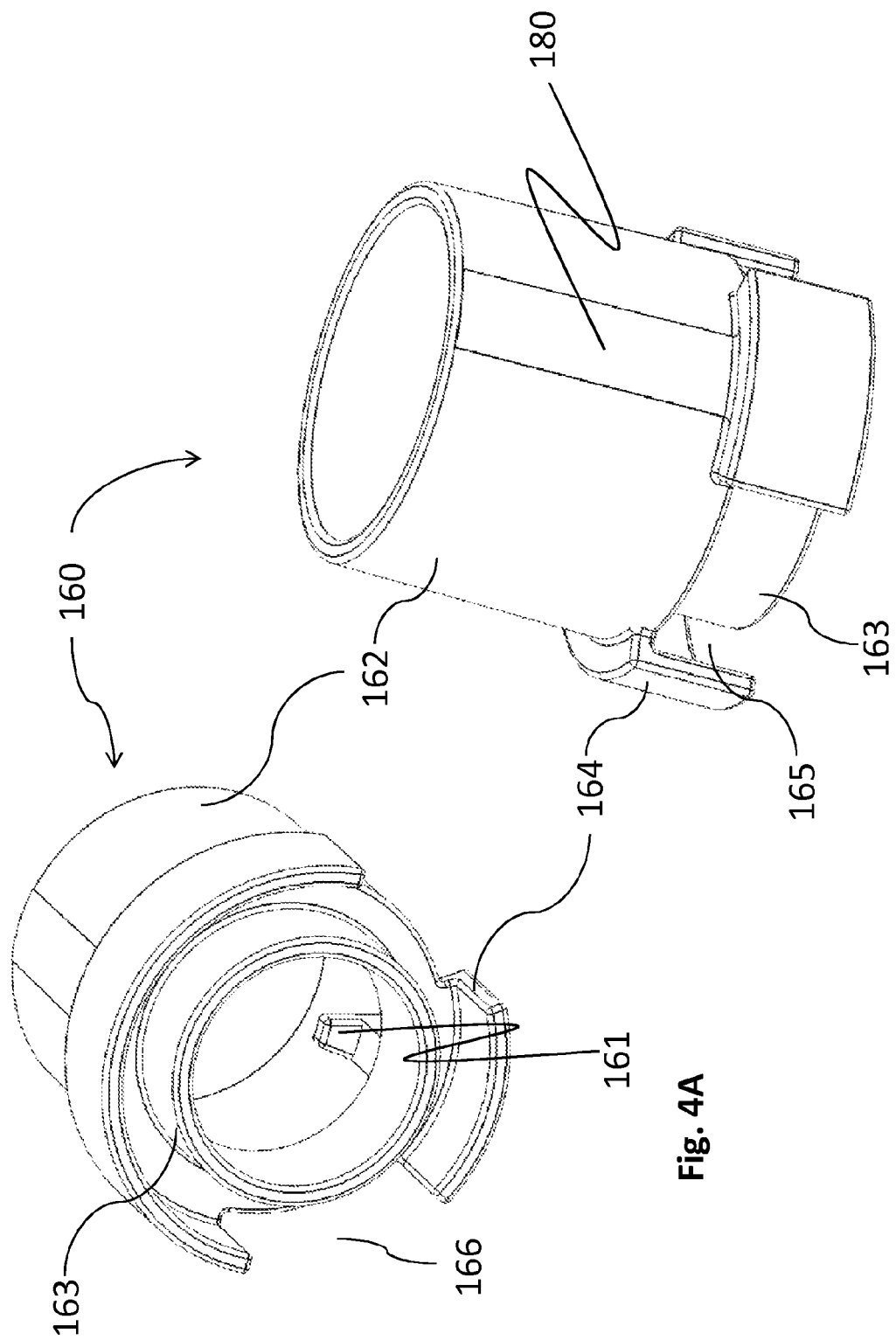
FIG. 4A is a detail perspective bottom view of an example of a movable indicator member.
FIG. 4B is a detail perspective side view of FIG. 4A.

FIG. 4A is a detail perspective bottom view of the indicator member 160 illustrating the third guiding means 161, which is a radial inward protrusion. In the illustrated example, the movable indicator member 160 comprises a distal tubular part 162 and a proximal tubular part 163 connected to each other and wherein the proximal tubular part 163 has a diameter which is lesser than the diameter of the distal tubular part 162, and annular L-shaped parts 164 arranged on the proximal annular end of the distal tubular part 162 forming an annular channel 165 and cut-outs 166. The distal tubular part 162 is adapted to be positioned within the first annular channel of the tubular distal housing part 152. FIG. 4B is a detail perspective side view of the indicator member 160 illustrating the indicator means 180, which in an exemplary embodiment of the invention are colour markings; where e.g. a red strip indicates when the plunger rod is in a non-ready-to-use position and e.g. a green strip indicates when the plunger rod is in a ready-to-use position. An alternative is to have the indicator means comprising a coloured flexible protrusion (not illustrated) that may penetrate through the window/opening 157 enabling a tactile and a visual indication of respective position.

Figure 5:
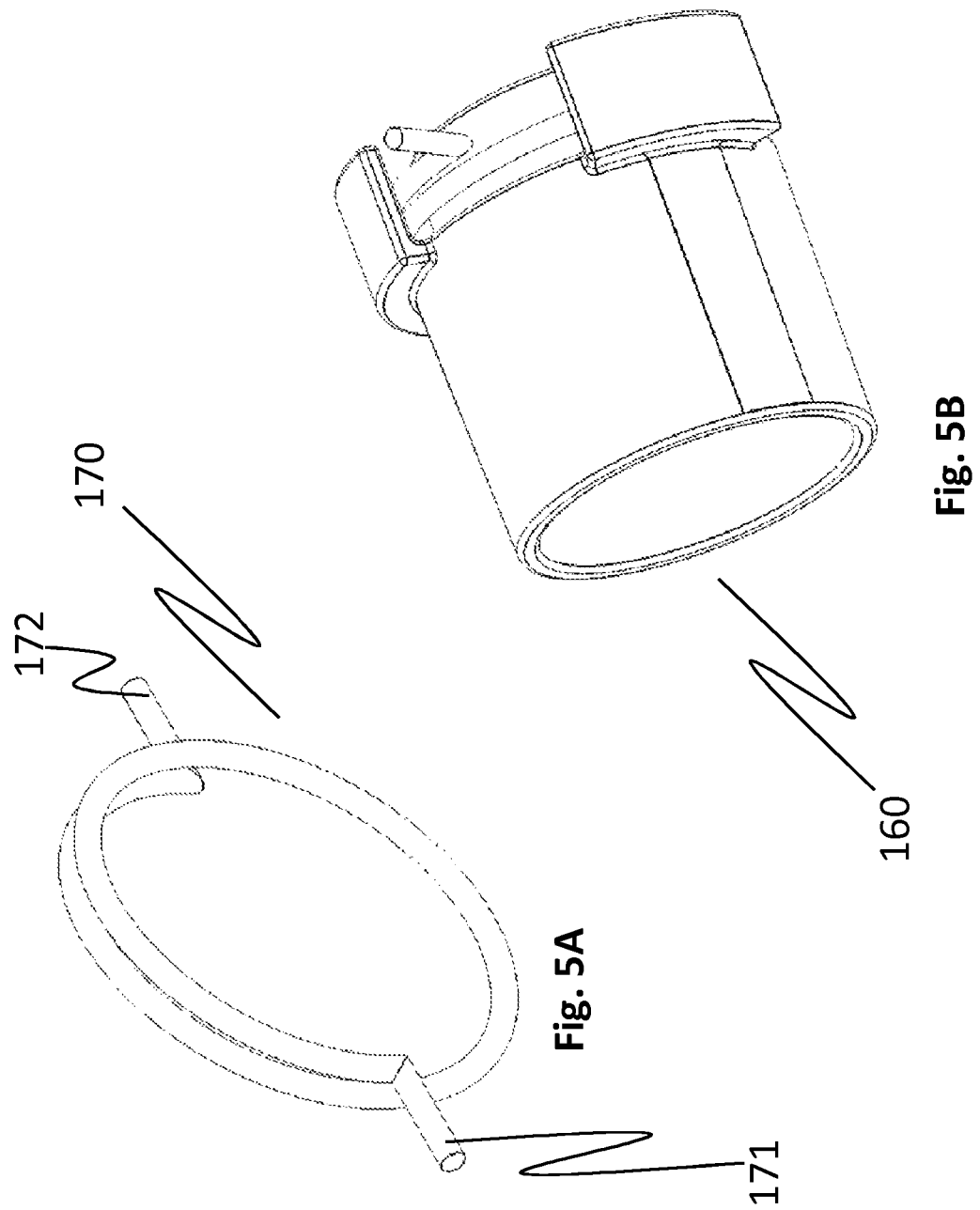
FIG. 5A illustrates an example of a resilient member.
FIG. 5B illustrates the resilient member of FIG. 5A and the movable indicator member of FIGS. 4A and 4B.

FIG. 5A illustrates an example of the resilient member 170 showing the first 171 and the second 172 ends for enabling an interaction between the indicator member 160 and the tubular distal housing part 152. In a preferred example of the invention the resilient member 170 is a torsion spring. FIG. 5B illustrates the resilient member 170 coupled to the indicator member 160. The resilient member 170 is arranged on the annular channel 165 of the movable indicator member 160 and each end of the resilient member 170 extends radial outwardly through a corresponding cut-out 166 of the indicator member 210. The second end 172 of the resilient member 170 being fixedly connected to the shield member 153 of either the tubular distal housing part 152 or the tubular proximal housing part 151, and the first end 171 of the resilient member 170 being arranged to interact with the annular L-shaped parts 164 of the indicator member.

Figure 6:
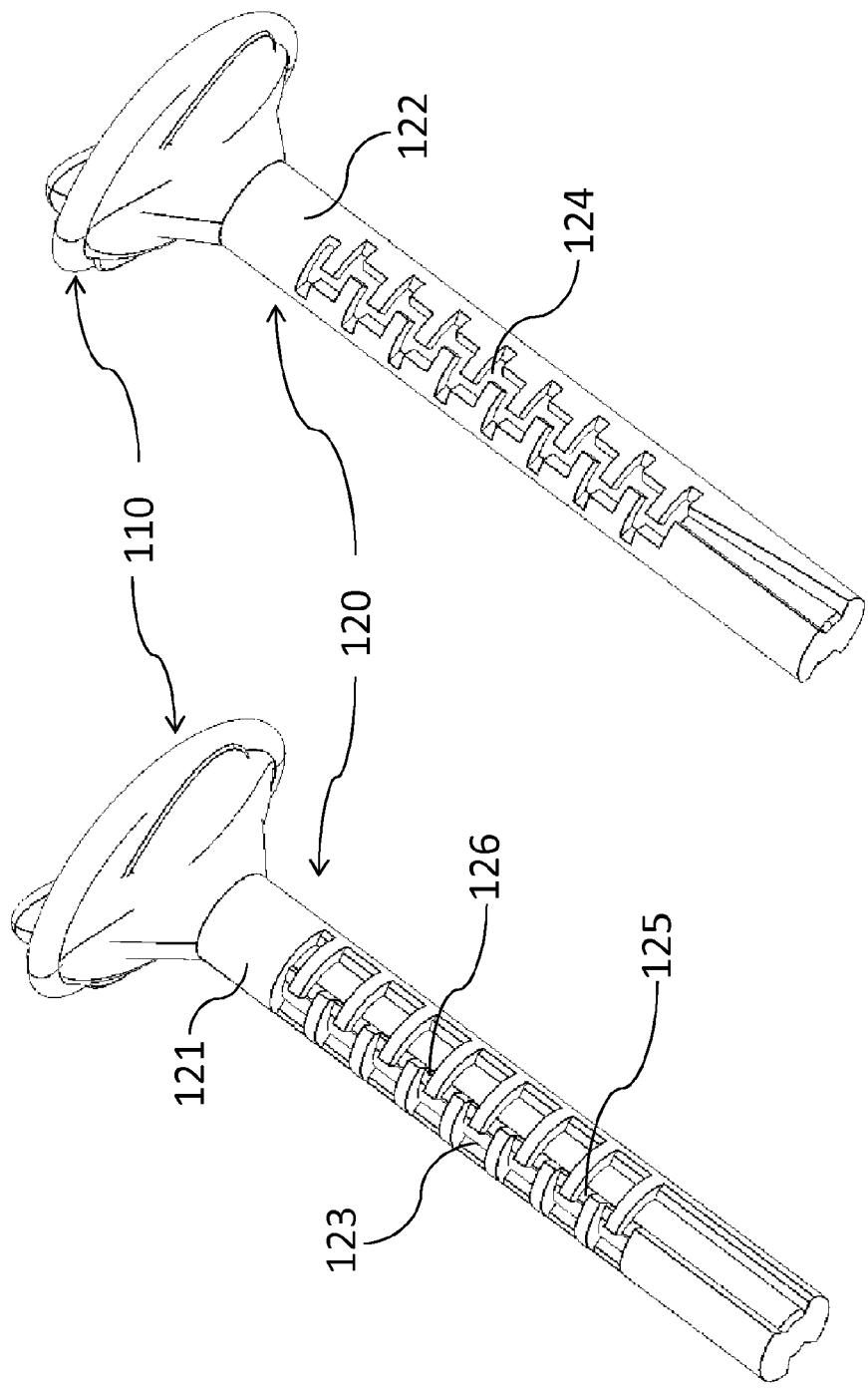
FIG. 6A is a detail perspective view of an example of a plunger rod.
FIG. 6B is a detail perspective side view of FIG. 6A rotated 180°.

FIGS. 6A and 6B illustrate an example of the plunger rod 120. The plunger rod 120 is a main elongated body having an outer circumferential surface with a pre-determined diameter and has a proximal and a distal end. The plunger rod comprises the actuator member 110 integrally attached to its distal end. The outer circumferential surface of the plunger rod is divided into a first 121 and second 122 circumferential halves surfaces wherein the first guiding means 123 is arranged on the first circumferential half surface 121 and wherein fourth guiding means 124 is arranged on the second circumferential half surface 122 which is located opposite to the first guiding means. The first and fourth guiding means are formed by distinct axially extending grooved and staggered tracks formed by alternating axial sections and circumferential sections extending in radial planes, said axial sections corresponding to the ready-to-use positions. Further, each axially extending grooved and staggered track form a continuous square wave pattern track. Wedge shaped elevations 125 having axially extending stop surfaces 126 are positioned on the circumferential sections of the first guiding means 123. As seen in FIG. 6B, the length of each circumferential section of the fourth guiding means 124 is half the predetermined length of each circumferential section of the first guiding means 123, and the length of the axial sections in both the first and the forth guiding means is the same. The predetermined length of the axial sections corresponds to a precise volume of medicament to be expelled when the plunger rod is axially displaced said predetermined length. Further, the proximal end of the plunger rod 120 is arranged to contact the stopper 131 within the medicament container.

Figure 7:
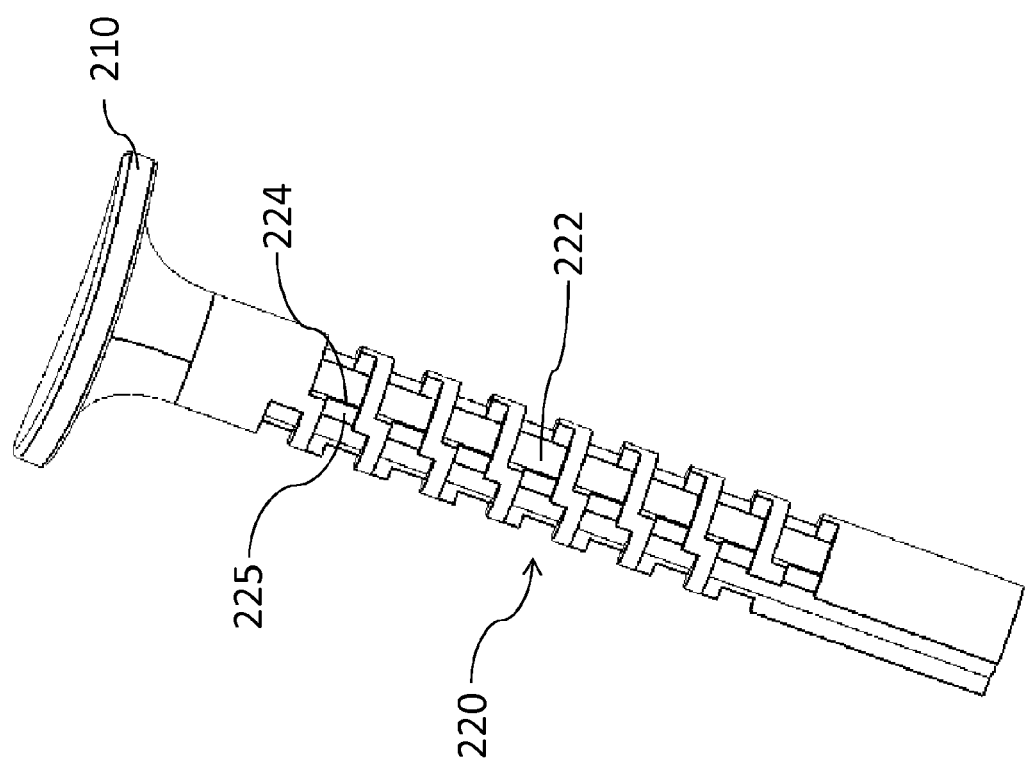
FIG. 7 is a detail perspective view of another example of a plunger rod.

FIG. 7 illustrates another example of the plunger rod 220. The plunger rod 220 is a main elongated body having an outer circumferential surface with a pre-determined diameter, a proximal end and a distal end. The plunger rod 220 comprises the actuator member 210 integrally attached to its distal end. On the outer surface of the plunger rod, the first and fourth guiding means are formed by a single axially extending grooved and staggered track 222 formed by alternating axial sections and circumferential sections extending in radial planes, said axial sections corresponding to the ready-to-use positions. Wedge shaped elevations 225 having axially extending stop surfaces 224 are positioned on the circumferential sections of the single axially extending grooved and staggered track 222. The predetermined length of the axial sections corresponds to a precise volume of medicament to be expelled when the plunger rod is axially displaced said predetermined length. Further, the proximal end of the plunger rod 220 is arranged to contact the stopper 131 within the medicament container.

In a first embodiment of the invention, the disclosed plunger rod 120 of FIGS. 6A, 6B is to be used with the housing 150 as disclosed in FIGS. 3A, 3B, with the movable indicator member as disclosed in FIGS. 4A, 4B, and with the resilient member as disclosed in FIGS. 5A, 5B. In the first embodiment, the second guiding means 154 of the housing is arranged to interact with the first guiding means 123 i.e. the first axially extending grooved and staggered track, and the third guiding means 161 of the indicator member 160 is arranged to interact with the fourth guiding means 124 i.e. the second axially extending grooved and staggered track. When the plunger rod 120 is in a non-ready-to-use position, both the second 154 and the third 161 guiding means are positioned in one of the respective circumferential sections such that the plunger rod 120 is disabled to be axially and proximally displaced. When the plunger rod 120 is rotated in one predetermined direction, the plunger rod is displaced from a non-ready-to use position to a ready-to-use position such that the second guiding means 154 moves within one of the circumferential sections of the first guiding means 123 over one of the wedge shaped elevations 125 until said second guiding means is positioned in one of the axial sections of the first guiding means and abutting the stop surface 126 of the wedge shaped elevation such that the plunger rod 120 is disable to be rotated in the opposite direction. The third guiding means 161 of the indicator member 160 is also displaced within one of the circumferential sections of the fourth guiding means 124 until said third guiding means is positioned in one of the axial sections of the forth guiding means. Since the length of each circumferential section of the fourth guiding means 124 is half the predetermined length of each circumferential section of the first guiding means 123, the indicator member 160 is forced to rotate in relation to the housing 150, i.e. the movable indicator member is moved from a first angular position indicating that the plunger rod is in a non-ready-to-use position to a second angular position indicating that the plunger rod is in a ready-to-use position by the interaction between the third guiding means 161 and one axially extending wall of the fourth guiding means. The indication of the first and second angular position is achieved by the indicator means 180 of the indicator member 160 through the opening/window 157 of the housing 150 for giving an indication to a user of the device that a predetermined dose of medicament can be expelled. At the same time, the at least one resilient member 170 is stressed to accumulate a force. When the plunger rod 120 is axially and proximally displaced, both the second guiding means 154 of the housing and the third guiding means 161 of the indicator member 160 are displaced within the respective axial section until said second 154 and third 161 guiding means are positioned in a subsequent respective circumferential section. When the third guiding means 161 of the indicator member 160 reaches the subsequent circumferential section of the fourth guiding means, the accumulated force in the at least one resilient member 170 forces the indicator member 160 to be moved back to the first angular position indicating that the plunger rod is in a subsequent non-ready-to-use position. The procedure as disclosed above can be repeated until the second guiding means 154 of the housing reaches the end of the first guiding means 123 i.e. the first axially extending grooved and staggered track and/or the medicament container is emptied. Since the plunger rod 120 cannot be reversed due to the interaction between the second guiding means 154 and the stop surfaces 126 of the wedge shaped elevations 125, the device is then expended. It has to be observed that in the first embodiment for delivering a predetermined dose of medicament, the plunger rod 120 is rotated in relation to the housing in one direction such that the indicator member is moved from the first angular position to the second position. Then, for delivering another predetermined dose of medicament the plunger rod 120 is rotated in relation to the housing in an opposite direction.

In a second embodiment of the invention, the disclosed plunger rod 220 of FIG. 7 is to be used with the housing 150 as disclosed in FIGS. 3A, 3B; with the indicator member as disclosed in FIGS. 4A, 4B; and with the resilient member as disclosed in FIGS. 5A, 5B. In the second embodiment, both the second 154 and the third 161 guiding means are arranged to interact with the single axially extending grooved and staggered track 222. When the plunger rod 220 is in a non-ready-to-use position, the third guiding means 161 of the indicator member 160 is positioned in a circumferential section of the the single axially extending grooved and staggered track 222 and the second guiding means 154 of the housing is positioned in a subsequent circumferential section of the the single axially extending grooved and staggered track 222 such that the plunger rod 220 is disabled to be axially and proximally displaced. When the plunger rod 220 is rotated in relation to the housing in a clock-wise direction, both the second 154 and the third 161 guiding means are displaced within the respective circumferential section of the the single axially extending grooved and staggered track 222 over one of the wedge shaped elevations 225 until said second 154 and said third 161 guiding means are positioned in a respective axial section. The second guiding means 154 of the housing then abuts the stop surface 224 of the wedge shaped elevation 225 such that the plunger rod 220 is disable to be rotated in the counter clock-wise direction. The third guiding means 161 of the indicator member 160 abuts then an axially extending wall of the single axially extending grooved and staggered track 222 such that the indicator member 160 is forced to rotate in relation to the housing 150 from a first angular position indicating that the plunger rod is in a non-ready-to-use position to a second angular position indicating that the plunger rod is in a ready-to-use position. The indication of the first and second angular position is achieved by the indicator means 180 of the indicator member 160 through the opening/window 157 of the housing 150 for giving an indication to a user of the device that a predetermined dose of medicament can be expelled. At the same time, the at least one resilient member 170 is stressed to accumulate a force. When the plunger rod 220 is axially and proximally displaced, both the second guiding means 154 of the housing and the third guiding means 161 of the indicator member 160 are displaced within the respective axial section until said second 154 and third 161 guiding means are positioned in a subsequent respective circumferential section. When the third guiding means 161 of the indicator member 160 reaches the subsequent circumferential section of the of the single axially extending grooved and staggered track 222, the accumulated force in the at least one resilient member 170 forces the indicator member 160 to be moved back to the first angular position indicating that the plunger rod is in a subsequent non-ready-to-use position. The procedure as disclosed above can be repeated until the second guiding means 154 of the housing reaches the end of the axially extending grooved and staggered track 222 and/or the medicament container is emptied. Since the plunger rod 220 cannot be reversed due to the interaction between the second 154 and third 161 guiding means with the stop surface 224 of the wedge shaped elevation 225 respectively, the device is then expended. It has to be observed that in the second embodiment for delivering a predetermined dose of medicament, the plunger rod 220 is rotated in relation to the housing only in a clock-wise direction.

A further advantage of the present invention is that in case that the second guiding means 154 of the housing breaks, the third guiding means 161 of the movable indicator member 160 may serve as a backup/support for the second guiding means.

The present invention is not limited to the above-described embodiments since various alternatives, modifications and equivalents may be used. Therefore, the above embodiments should not be taken as limiting the scope of the invention, which is defined by the appended claims.

The invention claimed is:

1. A medicament delivery device, comprising:
an elongated housing extending along an axis for containing a medicament;
a coaxially extending plunger rod mounted in the housing so as to be axially displaceable for expelling successive doses of medicament and rotatable about the axis;
wherein the plunger rod and housing respectively comprise first and second guides in mutual engagement that are configured to guide the plunger rod in the housing successively from a ready-to-use position, in which the plunger rod is axially displaceable for expelling a dose of medicament, to a non-ready-to use position, in which the plunger rod is axially blocked, the non-ready-to use position being axially spaced from the ready-to-use position, and from the non-ready-to use position to a subsequent ready-to-use position angularly spaced from the non-ready-to use position about the axis;
wherein the second guide is integral with the housing;
an indicator member displaceably mounted on the housing between a first angular position indicative of the ready-to-use positions and a second angular position indicative of the non-ready-to use position and subsequent ready-to-use position, the indicator member and plunger rod respectively comprising third and fourth guides in direct mutual engagement, whereby the position of the indicator member is linked to the position of the plunger rod;

wherein the first and fourth guides include alternating axial sections and circumferential sections extending in radial planes.

2. The medicament delivery device of claim 1, wherein the indicator member comprises indicator means on its outer surface for enabling visual and/or audible and/or tactile indication through a window/opening on the housing when the plunger rod is in the ready-to-use positions or in the non-ready-to-use position; and the third guide is integral with the indicator member.

3. The medicament delivery device of claim 2, wherein the indicator means comprises at least one of a color mark and a flexible protrusion.

4. The medicament delivery device of claim 3, wherein the indicator member is resiliently connected to the housing through at least one resilient member which comprises a first end connected to the indicator member and a second end connected to the housing.

5. The medicament delivery device of claim 4, wherein the indicator is mounted onto the housing such that the indicator member is rotatable about the axis between the first angular position indicative of the ready-to-use positions and the second angular position indicative of the non-ready-to-use positions, the indicator member being biased by the resilient member into the second angular position.

6. The medicament delivery device of claim 5, wherein the second guide includes at least one inward radial extending protrusion, and the third guide includes at least one inward radial extending protrusion.

7. The medicament delivery device of claim 6, wherein the third guide is configured to substitute for the second guide.

8. The medicament delivery device of claim 7, wherein the axially displaced distance of the plunger rod between a ready-to-use position and a non-ready-to-use position corresponds to a precise volume of medicament to be expelled.

9. The medicament delivery device of claim 8, wherein the first and fourth guides include distinct axially extending grooved and staggered tracks, the axial sections corresponding to the ready-to-use positions.

10. The medicament delivery device of claim 9, wherein the plunger rod comprises an outer circumferential surface divided into first and second circumferential half surfaces, the first guide is arranged on the first circumferential half surface, and the fourth guide is arranged opposite the first guide on the second circumferential half surface.

11. The medicament delivery device of claim 10, wherein each axially extending grooved and staggered track forms a continuous square-wave pattern.

12. The medicament delivery device of claim 8, wherein the first and fourth guides include a single axially extending grooved and staggered track, the axial sections corresponding to the ready-to-use positions.

13. The medicament delivery device of claim 12, wherein the plunger rod comprises an outer circumferential surface, and the single axially extending grooved and staggered track is continuously arranged around the outer circumferential surface.

14. The medicament delivery device of claim 13, wherein the single axially extending grooved and staggered track has a continuous spiral stair pattern.

15. The medicament delivery device of claim 1, wherein the medicament delivery device is an injection device.

16. The medicament delivery device of claim 4, wherein the second guide includes at least one inward radial extending protrusion, and the third guide includes at least one inward radial extending protrusion.

17. The medicament delivery device of claim 16, wherein the third guide is configured to substitute for the second guide.

18. The medicament delivery device of claim 17, wherein the axially displaced distance of the plunger rod between a ready-to-use position and a non-ready-to-use position corresponds to a precise volume of medicament to be expelled.

19. The medicament delivery device of claim 18, wherein the first and fourth guides include distinct axially extending grooved and staggered tracks, the axial sections corresponding to the ready-to-use positions.

20. The medicament delivery device of claim 18, wherein the first and fourth guides include a single axially extending grooved and staggered track, the axial sections corresponding to the ready-to-use positions.

* * * * *